United States Patent [19]

Simon et al.

[11] Patent Number: 4,650,790

[45] Date of Patent: Mar. 17, 1987

[54] DRUG COMBINATIONS HAVING SYNERGISTIC EFFECT

[75] Inventors: Ferenc Simon; Attila Romváry; János Varga; László Bozzay, all of Budapest; Edit Brückner née Gábor, Pápa, all of Hungary

[73] Assignee: Patentbureau Danubia, Hungary

[21] Appl. No.: 717,157

[22] Filed: Mar. 28, 1985

[30] Foreign Application Priority Data

Mar. 28, 1984 [HU] Hungary .............................. 1225/84
Mar. 28, 1984 [HU] Hungary .............................. 1226/84
Apr. 20, 1984 [HU] Hungary .............................. 1527/84

[51] Int. Cl.$^4$ .............................................. A61K 31/71
[52] U.S. Cl. ........................................ 514/39; 514/35; 514/36; 514/37; 514/38; 514/40; 514/41
[58] Field of Search ....................... 514/36, 37, 38, 39, 514/40, 41, 35

[56] References Cited

U.S. PATENT DOCUMENTS 2,799,620  7/1957  Waksman et al. ................. 536/13.2
2,931,798  4/1960  Umezawa et al. ................. 536/13.7
3,915,955 10/1975  Copper et al. .................... 536/13.6

FOREIGN PATENT DOCUMENTS 2072012  9/1981  United Kingdom .

Primary Examiner—Johnnie R. Brown
Assistant Examiner—Elli Peseler
Attorney, Agent, or Firm—Keil & Weinkauf

[57] ABSTRACT

The invention relates to a synergistic antibiotic composition useful for the treatment of respiratory, gastrointestinal or urinary infections and septicaemia of domestic animals. The composition comprises tiamulin hydrogen fumarate and an aminoglycoside antibiotic or a pharmaceutically acceptable salt thereof in a weight ratio of 5:1 to 1:5. The active components are admixed or diluted with a carrier, used in veterinary therapy, in a weight ratio of 1:1 to 1:50 and formulated for oral or parenteral application.

13 Claims, No Drawings

DRUG COMBINATIONS HAVING SYNERGISTIC EFFECT

This invention relates to new drug combinations having synergistic effect which cure and prevent diseases of protozoal and bacterial (*Treponema hyodysenteriae, Escherichia coli,* Pasteurella, Salmonella, Mycoplasma spp.) origin of cattle, calves, sheep, goats, swine, rabbits and poultry. Furthermore the invention relates to a process for the preparation of these drug combinations.

It is known that the greatest economical losses in swine and poultry flocks are due to diseases of the gastrointestinal tract and of respiratory organs. Losses appear not only because of increased mortality and costs of treatment but adversely affected performance, too.

Mycoplasma strains play a great part in the background of the disorders of the respiratory tract, but inflammatory signs due to secondary pathogens (e.g. Streptococcus, Staphylococcus, Pasteurella, Bordetella strains) are also important.

Diseases of the digestive organs are usually caused by the overgrowth of Gram negative pathogens in the intestinal tract, among them the most important is the invasion of *Escherichia coli* strains, which results in diarrhoe and oedema disease in swine herds and in coli septicaemia in poultry flocks.

The number of gynecological diseases of dams on large scale units is continuously increasing and subclinical disorders of the udder are more frequent. Mastitis is caused mainly by Streptococcus, Staphylococcus, *Escherichia coli* and Corynebacterium strains.

Infections of bacterial and protozoal origin have been most widely treated and prevented with antibiotics and their combinations.

As the choice of antibiotics widened, marked decrease of infectious diseases of bacterial and protozoal origin became possible.

Widespread use of antibiotics resulted in the development of resistant strains, against which the single antibiotics became ineffective. To avoid the development of resistance, antibiotics are generally used for short period of time and this is the reason of the production of newer and newer antibiotics for increasingly greater costs.

Tiamulin (14-desoxy-14-[(2-diethyl-amino-ethyl)-mercapto-acetoxy]-mutilin hydrogen fumarate is a relatively new antibiotic in veterinary therapy. It has been found effective against some Gram positive bacteria, Mycoplasma and the most important Treponema.

Orally applied tiamulin is extremely effective against *Treponema hyodysenteriae* (British patent specification No. 2,072,012), which causes swine dysentery, and against *Mycoplasma hyopneumoniae* which causes enzootic pneumonia (Taylor, D. J., IPVS Congress, Mexico, 1982).

The application of tiamulin in combination with antihelminthics (tetramisole, levamisole, fenbendasole, parbendasole, piperazine and dichlorvos) has already been studied. Toxicity and compatibility of the combinations was investigated, too. There is no known combination of tiamulin with antibiotics until now.

It is the object of the present invention to produce drug combinations of known antibiotics which, beside considerable reduction of expenses, will include the individual effects of two or more components in a synergistic way.

The aminoglycoside antibiotics (streptomycin, neomycin, kanamycin, gentamicin, tobramycin, spectinomycin, apramycin etc.) are used in the treatment of acute and chronic infections of the respiratory organs, gastro-intestinal and urogenital tract, caused by Gram negative bacteria, Staphylococci and *Corynebacterium pyogenes*. However, according to literary data the aminoglycoside antibiotics are effective against Gram positive germs, too (*Staphylococcus aureus, Staphylococcus albus,* Corynebacterium strains, Aerobacter, Salmonella, Proteus, Neiseria, Pasteurella spp.).

The single or combined use of streptomycin and neomycin is widespread in the veterinary therapy for treating infections of various kinds.

Streptomycin alone or in combination with penicillin (Stredipen inj.) is primarily used for parenteral therapy of respiratory diseases.

The combination of neomycin with oxytetracycline is used in the treatment of mastitis, and enclosed in capsules it is available for intrauterin application.

Parenteral use of neomycin is limited because of its nephrotoxic properties. It may cause azotaemia and oliguria (Deutsche Med. Wschr. 104, 1783–1787/1979/).

Kanamycin alone or in combination with procaine-penicillin, dihydrostreptomycin, neomycin is applied mainly parenterally (im., iv., sc., intrauterine or intracysternally).

Tobramycin's and spectinomycin's main range of effectivity is against Gram negative pathogens (*E. coli,* Proteus, Klebsiella, Pseudomonas). They may be applied both orally and parenterally.

Apramycin's indications are coli-diarrhoea, oedema disease, swine-dysentery (Antimicrob. Chemother. 3, 609–613/1977/), retention of fetal membrane, metritis, pneumonia, fowl cholera, respiratory diseases and coli septicaemia of poultry. Apramycin acts favourably in the treatment of mastitis of cows caused by Gram negative and Gram positive pathogens, and it may be used for the treatment of MMA (metritis-mastitis-agalactia) syndrome of sows. It posseses particularly strong effect against Pseudomonas strains of mastitic origin.

Due to resistance patterns, combinations of apramycin with other chemotherapeutics have been developed. Such a combination is described in the Belgian patent specification No. 886,765, in which aminoglycoside antibiotics (apramycin, tobramycin, nebramycin) together with macrolides (tylosin, spiramycin, oleandomycin) are proposed against colibacillosis and Mycoplasma infections.

We carried out experiments to investigate the effect of aminoglycoside antibiotics and tiamulin against pathogen strains cultured from diseased animals. The invention is based on the recognition that when tiamulin hydrogen fumarate is applied in combination with an aminoglycoside antibiotic (streptomycin, neomycin, kanamycin, tobramycin, spectinomycin, apramycin, gentamycin) beside the fact that the spectrum of activity of the components is broadened, a more than additive, that is synergistic, interaction develops and this results in unexpectedly low antibacterial concentrations of the components.

Accordingly, the invention relates to new synergistic antibiotic compositions useful for the treatment of respiratory or urinary infections and septicaemia of domestic animals, comprising the antibiotic tiamulin hydrogen fumarate and an aminoglycoside antibiotic or a pharmaceutically acceptable salt thereof in a weight ratio of 5:1 to 1:5, admixed with inert, non toxic carriers used in veterinary therapy.

The synergistic activity of the combinations of the invention can be demonstrated in microbiological assays. For better understanding, the same field isolates of pathogens were used as test organisms. Minimal inhibiting concentrations (MIC) and minimal bactericide concentrations (MBC) of tiamulin and the aminoglycosides were determined.

The following Tables list the data of the microbiological survey and prove synergism.

As shown in the Tables, all the test organisms were controlled at highly reduced concentrations when any of the tiamulin-aminoglycoside combinations was used. The grade of intensification of the antimicrobial effect is of 4 to 8 times and it can reach the 200 to 400 times value in vitro. This means that the growth of the strains is inhibited even with considerably reduced doses.

The MIC and MBC values were measured in μg/ml units.

TABLE I

Intensification of the Antibacterial Activity of the 1:1 Ratio by Weight Combination of Tiamulin and Streptomycin

| Test Organism | Tiamulin MIC | Tiamulin MBC | Streptomycin MIC | Streptomycin MBC | Combination MIC | Combination MBC | Grade of Intensification |
|---|---|---|---|---|---|---|---|
| Staphylococcus aureus | 25 | 100 | 10 | 25 | 5 | 5 | 4–40 x |
| E. coli (Swine) | 50 | 100 | 100 | >200 | 50 | >200 | 2–4 x |
| E. coli (Calf) | >200 | >200 | 200 | >200 | 50 | >200 | 2–8 x |
| Salmonella typhi-murium | 200 | >200 | 50 | 200 | 50 | >200 | 2–8 x |
| Pasteurella multocida | 25 | 25 | 25 | 25 | 10 | 25 | 2–5 x |

TABLE II

Intensification of the Antibacterial Activity of the 1:1 Ratio by Weight Combination of Tiamulin and Neomycin

| Test Organism | Tiamulin MIC | Tiamulin MBC | Neomycin MIC | Neomycin MBC | Combination MIC | Combination MBC | Grade of Intensification |
|---|---|---|---|---|---|---|---|
| Staphylococcus aureus | 25 | 100 | 10 | 25 | 1 | 5 | 10–50 x |
| E. coli (Swine) | 50 | 100 | 5 | 10 | 5 | 5 | 2–40 x |
| E. coli (Calf) | >200 | >200 | >200 | >200 | 100 | 200 | 2–4 x |
| Salmonella typhi-murium | 200 | >200 | 10 | 25 | 5 | 5 | 4–80 x |
| Pasteurella multocida | 25 | 25 | 1 | 5 | <0.5 | <0.5 | 4–100 x |

TABLE III

Intensification of the Antibacterial Activity of the 1:1 Ratio by Weight Combination of Tiamulin- and Kanamycin

| Test Organism | Tiamulin MIC | Tiamulin MBC | Kanamycin MIC | Kanamycin MBC | Combination MIC | Combination MBC | Grade of Intensification |
|---|---|---|---|---|---|---|---|
| Staphylococcus aureus | 25 | 100 | 10 | 10 | 1 | 1 | 20–200 x |
| E. coli (Swine) | 50 | 100 | 10 | 25 | 5 | 5 | 4–40 x |
| E. coli (Calf) | >200 | >200 | >200 | >200 | 50 | 100 | 4–8 x |
| Salmonella typhi-murium | 200 | >200 | 25 | 50 | 1 | 5 | 20–400 x |
| Pasteurella multocida | 25 | 25 | 5 | 5 | <0.5 | <0.5 | 20–100 x |

TABLE IV

Intensification of the Antibacterial Activity of the 1:1 Ratio by Weight Combination of Tiamulin and Tobramycin

| Test Organism | Tiamulin MIC | Tiamulin MBC | Tobramycin MIC | Tobramycin MBC | Combination MIC | Combination MBC | Grade of Intensification |
|---|---|---|---|---|---|---|---|
| Staphylococcus aureus | 25 | 100 | <0.5 | 1 | <0.5 | 1 | 2–200 x |
| E. coli (Swine) | 50 | 100 | 1 | 5 | 1 | 5 | 2–100 x |
| E. coli (Calf) | >200 | >200 | 5 | 10 | 5 | 10 | 2–80 x |
| Pasteurella multocida | 25 | 25 | 1 | 5 | 1 | 5 | 2–50 x |
| Salmonella typhi-murium | 200 | >200 | 5 | 10 | 1 | 5 | 4–400 x |

TABLE V

Intensification of the Antibacterial Activity of the 1:1 Ratio by Weight Combination of Tiamulin-Spectinomycin

| Test Organism | Tiamulin MIC | Tiamulin MBC | Spectinomycin MIC | Spectinomycin MBC | Combination MIC | Combination MBC | Grade of Intensification |
|---|---|---|---|---|---|---|---|
| Staphylococcus aureus | 25 | 100 | 100 | 200 | 1 | 10 | 20–200 x |
| E. coli (Swine) | 50 | 100 | 25 | 25 | 1 | 25 | 2–20 x |
| E. coli (Calf) | >200 | >200 | >200 | >200 | 50 | >200 | 2–8 x |
| Salmonella thyphi-murium | 200 | >200 | 50 | 200 | 50 | 100 | 2–8 x |
| Pasteurella multocida | 25 | 25 | 10 | 25 | 5 | 10 | 4–10 x |

TABLE VI

Intensification of the Antibacterial Activity of the 1:1 Ratio by Weight Combination of Tiamulin and Apramycin

| Test Organism | Tiamulin | | Apramycin | | Combination | | Grade of Intensification |
|---|---|---|---|---|---|---|---|
| | MIC | MBC | MIC | MBC | MIC | MBC | |
| Staphylococcus aureus | 25 | 100 | 10 | 25 | 1 | 5 | 10–50 x |
| E. coli (Swine) | 50 | 100 | 25 | 25 | 5 | 10 | 5–20 x |
| E. coli (Calf) | >200 | >200 | >200 | >200 | 5 | 10 | 40–80 x |
| Salmonella typhi-murium | 200 | >200 | 10 | 10 | 5 | 5 | 4–80 x |
| Pasteurella multocida | 25 | 25 | 10 | 25 | <0.5 | <0.5 | 40–100 x |

TABLE VII

Intensification of the Antibacterial Activity of the 1:1 Ratio by Weight Combination of Tiamulin and Gentamycin

| Test Organism | Tiamulin | | Gentamycin | | Combination | | Grade of Intensification |
|---|---|---|---|---|---|---|---|
| | MIC | MBC | MIC | MBC | MIC | MBC | |
| Staphylococcus aureus | 25 | 100 | 0.5 | 5 | <0.5 | 5 | 2–100 x |
| E. coli (Swine) | 50 | 100 | 5 | 5 | 5 | 5 | 2–40 x |
| E. coli (Calf) | >200 | >200 | 5 | 5 | 5 | 5 | 2–80 x |
| Salmonella typhi-murium | 200 | >200 | 5 | 5 | 5 | 5 | 2–80 x |
| Pasteurella multocida | 25 | 25 | <0.5 | 1 | <0.5 | 5 | 2–100 x |

Because of their synergistic properties, the preparations of the invention may be applied in lower and more economic doses. As a result of the broadened range of spectrum, the combinations can be succesfully used in the therapy of respiratory and gynecological diseases owing to mycoplasma and secondary bacterial complications.

Further advantage of the combinations according to the invention is the reduced possibility of development of toxic-side-effects and the shortening of the necessary withdrawal period to prevent drug residues in edible tissues. These advantages originate from the reduced doses of aminoglycosides in the combinations.

The preparations of the invention can be produced according to known technics, that is the active ingredients are mixed with or dissolved in carriers used in veterinary therapy.

The formulation of the preparate is chosen according to the given case. It may be applied orally, mixed to the feed or in the drinking water, mainly in large scale units, or parenterally for individual or mass treatment.

The parenteral application may be intramuscular, intrauterin or intracysternal. The preparation for parenteral use is spread on a carrier, preferably lactose, in 1:1 to 1:50 ratio by weight, and then it is dissolved in a suitable solvent, preferably water, dimethyl formamid or vegetable oil, in a 1:1 to 1:25 ratio by weight. An oral dose of 10 mg/kg body weight of this combination of tiamulin hydrogen fumarate and an aminoglycoside antibiotic is adequate for prevention and treatment of gastroenteritis caused by Gram negative agents.

Favourable effects can be reached with orally administered preparations in cases of E. coli, Klebsiella and Salmonella infections, too.

In an im. dose of 10 mg/kg body weight the preparation can be used to cure bronchopneumonia and Pasteurellosis, listeriosis and staphylococcus infections of all species of animals.

A dose of 5.0 g/animal given intrauterinally can be used for the prevention of metritis after calving or to cure retention of fetal membrane.

A 0.5 g dose of the active ingredient/quarter udder infused intracysternally prevents not only mastitis owing to Gram positive and Gram negative bacteria but also of mycoplasma origin.

The invention is further illustrated by the following examples without limiting, however, the scope claimed to these examples.

EXAMPLE 1

2.5 g of tiamulin hydrogen fumarate and 2.5 g of streptomycin sulfate are filled into an intrauterin capsule.

One capsule is put daily into the uterus of cows.

25 cows were treated immediately after calving. Rapid involution and cessation of uterinal discharge occurred within 24 hours.

EXAMPLE 2

0.1 g of tiamulin hydrogen fumarate and 0.5 g of neomycin sulfate are dissolved in 10 ml of aqua destillata for injection.

This solution is infused intracysternally once daily via the teat canal into the thoroughly outmilked quarter.

5 dairy cows suffering of mastitis were treated with 10 ml of this preparation for 3 days. The antibiotic was infused into the udder through the teat canal. Clinical status and secretion became normal. The result of microbiological examination was negative.

EXAMPLE 3

1.0 g of tiamulin hydrogen fumarate and 0.2 g of kanamycin sulfate were dissolved in 10 ml of water for injection.

This solution is injected intramuscularly once daily in a dose of 1 ml per 10 kg of body weight.

15 weaned pigs (average body weight: 12 to 15 kg) suffering of pyogenic dermatitis were treated intramuscularly for 3 days. One week after the last treatment the skin of the animals healed and crusts disappeared.

EXAMPLE 4

200.0 g of tiamulin hydrogen fumarate, 100.0 g of apramycin sulfate and 700.0 g of lactose are homogenized and 0.2 g of the preparation is dissolved in 1 l of drinking water of animals. The treatment is continued for 5 days.

350 hogs, suffering of swine-dysentery were treated with the preparate dissolved in the drinking water. The animals readily accepted the medicated water. Signs of "bloody scours" disappeared by the second day, and clinical status of the animals became normal on the fourth day of the treatment.

EXAMPLE 5

1600.0 mg of tiamulin hydrogen fumarate, 400.0 mg of gentamicin sulfate and 3000.0 mg of lactose are homogenized. 5 g of the thus-obtained water soluble preparate are dissolved in 100 ml of tap water.

45 piglets in 5 litters were infected by *E. coli* diarrhoea. 0.5 ml/kg b.w. of the above solution was orally applied to the piglets from a needleless syringe. All the piglets became healthy after one treatment.

EXAMPLE 6

300.0 mg of tiamulin hydrogen fumarate and 100.0 mg of tobramycin sulfate are homogenized in 10.0 ml of oil for injection.

10 dairy cows suffering of mastitis of mixed infections origin (Streptococcus, Pseudomonas) were treated with this preparation which was infused into the thoroughly outmilked udder through the teat canal once per day. The udder and the milk became normal. No pathogens were detected in milk samples collected 1 week after the last treatment.

EXAMPLE 7

20.0 g of tiamulin hydrogen fumarate and 10.0 g of spectinomycin are homogenized in 70.0 ml of oil for injection.

24 calves suffering of *E. coli* diarrhoea were intramuscularly treated with this preparation in a dose of 1 ml/10 kg of b.w. for 3 days. Diarrhoea disappeared after the first injection and the milk consumption increased.

What we claim is:

1. A synergistic antibiotic composition comprising an effective amount of a combination of the antibiotic tiamulin hydrogen fumarate and an aminoglycoside antibiotic selected from the group consisting of streptomycin, neomycin, kanamycin, tobramycin, spectinomycin, apramycin and gentamycin or a pharmaceutically acceptable salt thereof in a weight ratio of 5:1 to 1:5, admixed with an acceptable inert, non-toxic carrier for veterinary therapy.

2. A composition as defined in claim 1 for the treatment of mastitis, comprising the antibiotic composition in a dosage unit of 150–500 mg/quarter udder.

3. A composition as defined in claim 1, comprising the antibiotic composition in a dosage unit of 2.5–5.0 mg/kg body weight for intrauterine application.

4. A composition as defined in claim 1, wherein the carrier is milk powder.

5. A composition as defined in claim 4, wherein the active ingredients and the milk powder are used in a weight ratio of 5:1 to 1:5.

6. The composition of claim 1, wherein water, vegetable oils or dimethyl formamid, is used as carrier.

7. The composition of claim 6, wherein the active ingredients and the carrier are used in a weight ratio of 1:10 to 1:25.

8. A method for treating respiratory infections in domestic animals which comprises treating said animals with an effective amount of a composition as defined in claim 1.

9. A method for treating urinary infections in domestic animals which comprises treating said animals with an effective amount of a composition as defined in claim 1.

10. A method for treating septicaemia in domestic animals which comprises treating said animals with an effective of a composition as defined in claim 1.

11. The method of claim 8, wherein the active ingredients and the carrier are used in a weight ratio of 1:10 to 1:25.

12. The method of claim 9, wherein the active ingredients and the carrier are used in a weight ratio of 1:10 to 1:25.

13. The method of claim 10, wherein the active ingredients and the carrier are used in a weight ratio of 1:10 to 1:25.

* * * * *

UNITED STATES PATENT AND TRADEMARK OFFICE
CERTIFICATE OF CORRECTION

PATENT NO. : 4,650,790

DATED : March 17, 1987

INVENTOR(S) : Ferenc SIMON et al.

It is certified that error appears in the above-identified patent and that said Letters Patent is hereby corrected as shown below:

On the Title Page:

[73] Assignee:

[Patentbureau Danubia]

should be:

Hajdusagi Agraripari Egyesules, Naduvar

Signed and Sealed this

Twentieth Day of October, 1987

Attest:

DONALD J. QUIGG

Attesting Officer

Commissioner of Patents and Trademarks